US012569313B2

(12) United States Patent (10) Patent No.: US 12,569,313 B2
Polchin (45) Date of Patent: Mar. 10, 2026

(54) HANDS-FREE CONTROLLER FOR SURGICAL MICROSCOPE

(71) Applicant: Digital Surgery Systems, Inc., Goleta, CA (US)

(72) Inventor: George Polchin, Goleta, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 0 days.

(21) Appl. No.: 18/701,128

(22) PCT Filed: Oct. 17, 2022

(86) PCT No.: PCT/US2022/078213
§ 371 (c)(1),
(2) Date: Apr. 12, 2024

(87) PCT Pub. No.: WO2023/064954
PCT Pub. Date: Apr. 20, 2023

(65) Prior Publication Data
US 2024/0350224 A1 Oct. 24, 2024

Related U.S. Application Data

(60) Provisional application No. 63/256,479, filed on Oct. 15, 2021.

(51) Int. Cl.
*A61B 90/25* (2016.01)
*A61B 34/37* (2016.01)
(Continued)

(52) U.S. Cl.
CPC .............. *A61B 90/25* (2016.02); *A61B 34/37* (2016.02); *A61B 90/361* (2016.02);
(Continued)

(58) Field of Classification Search
CPC ...................................................... A61B 90/25
See application file for complete search history.

(56) References Cited

U.S. PATENT DOCUMENTS 4,912,388 A 3/1990 Tanaka et al.
4,989,253 A 1/1991 Liang et al.
(Continued)

FOREIGN PATENT DOCUMENTS

DE 19640907 A1 9/2005
EP 1400828 A 3/2004
(Continued)

OTHER PUBLICATIONS

International Search Report and Written Opinion mailed Feb. 27, 2023 for International Application Serial No. PCT/US2022/078213 filed on Oct. 17, 2022.

*Primary Examiner* — Irfan Habib
(74) *Attorney, Agent, or Firm* — K&L Gates LLP; Dennis A. Majewski

(57) ABSTRACT

Systems and methods are disclosed for controlling a surgical visualization system using a hands-free (e.g., mouth, nose, and breath actuated) controller. An example system includes a microscope camera associated with the surgical system; a controller of the microscope camera; a processor; and a memory storing instructions for the processor. The controller may be separate from the microscope camera, and may comprise one or more joysticks. In some aspects, the controller may further include a pressure detector configured to detect pressure within a tube of a joystick. Also or alternatively, the controller may include a keyed proximity sensor to activate the controller when a surgeon is present. The processor may be configured to: receive a movement input based on a movement of the joystick along a Cartesian
(Continued)

direction; and cause a corresponding movement of the microscope camera along the Cartesian direction.

8 Claims, 9 Drawing Sheets

(51) Int. Cl.
| | |
|---|---|
| *A61B 90/00* | (2016.01) |
| *H04N 23/50* | (2023.01) |
| *H04N 23/667* | (2023.01) |
| *H04N 23/695* | (2023.01) |
| *A61B 34/00* | (2016.01) |

(52) U.S. Cl.
CPC ......... *H04N 23/555* (2023.01); *H04N 23/667* (2023.01); *H04N 23/695* (2023.01); *A61B 2034/742* (2016.02); *A61B 2090/064* (2016.02)

(56) References Cited

U.S. PATENT DOCUMENTS

| | | | | |
|---|---|---|---|---|
| 11,896,328 | B1 * | 2/2024 | Roh | A61B 34/25 |
| 11,931,118 | B1 * | 3/2024 | Roh | A61B 34/25 |
| 11,998,281 | B1 * | 6/2024 | Roh | G16H 80/00 |
| 12,029,434 | B1 * | 7/2024 | Roh | G16H 40/63 |
| 12,269,180 | B2 * | 4/2025 | Faraji | B25J 9/1692 |
| 2004/0008181 | A1 | 1/2004 | Saylor et al. | |
| 2017/0173262 | A1 * | 6/2017 | Veltz | G16H 20/17 |
| 2019/0324252 | A1 * | 10/2019 | Mak | G02B 21/06 |
| 2022/0303435 | A1 * | 9/2022 | Ramirez Luna | H04N 23/51 |

FOREIGN PATENT DOCUMENTS

| | | | |
|---|---|---|---|
| EP | 1804151 | A | 7/2007 |
| EP | 2026111 | A1 | 2/2009 |
| WO | 2021/067597 | A1 | 4/2021 |
| WO | 2023/064954 | A1 | 4/2023 |

* cited by examiner

HANDS-FREE CONTROLLER FOR SURGICAL MICROSCOPE

PRIORITY CLAIM

The present application is a national phase entry of PCT Patent Application No. PCT/US2022/078213, filed on Oct. 17, 2022, which claims priority to and the benefit of U.S. Provisional Patent Application No. 63/256,479, filed on Oct. 15, 2021, the entirety of which is are incorporated herein by reference.

TECHNICAL FIELD

Certain aspects of the present disclosure generally relate to controls for surgical systems, and specifically relate to hands-free controls for surgical systems.

BACKGROUND

During surgery, a surgeon's hands are usually occupied with controlling surgical hand tools. Further, microsurgery often involves the use of a surgical microscope, which may involve fine control for positioning, orientation, and setting zoom/focus so that the surgeon can reliably see any aspect of a surgical site, quickly and efficiently during the procedure. The primary existing method of microscope control is via hand controls mounted directly to the microscope. Microscope adjustment is typically required continually throughout a surgical procedure. Yet, the use of hand controls can often distract the surgeon and negatively impact the surgery. For example, hand controls often cause the surgeon to interrupt the surgical procedure, free one or both hands (e.g., by removing instruments from the respective hands, and offloading said instruments from the surgical field), move their hand(s) to the microscope, perform the adjustment, move their hand(s) back into operating position, re-acquire the instrument(s), re-position the instrument(s) into the surgical field.

In some optical microscopes, where the primary visualization path for the surgeon is to look through oculars attached directly to the microscope, an optional mouthpiece accessory (also known as a mouth switch) may be used to control the microscope pose in a limited way. FIG. 1 shows a surgeon using his hands to adjust such a known mouthpiece. During use, the surgeon's hands are used to control surgical tools. To position the microscope without using the hands, the surgeon bites the mouthpiece flange, thereby activating a switch that unlocks the brakes on the microscope mount. This may enable the surgeon to position the microscope in a limited way, for example in X and Y pivot directions but not in Z linear direction, nor in any other angular directions. Another mode might allow Z linear movement only (thereby enabling fine continuous focus control for the surgeon in any part of the field of view where focus is possible.) Some modes might allow such motions simultaneously or full six degree of freedom motion.

However, such conventional surgical systems that use mouth switches are hugely inconvenient and distracting for surgeons, which impact surgical performance. For example, such systems involve having a mouth switch near the surgeon's face for long periods of time during a surgical procedure, forcing a rigid object uncomfortably into their mouth or nearby. Furthermore, surgeons may be required to tensely grip the mouth switch by their teeth, causing additional inconvenience. Conventionally, a mouth controller such as the mouth switch (e.g., as shown in FIG. 1) is intrusive hard switch that the surgeon has to bite down upon and keep in their mouth for the duration of use. This requires surgeons to use their jaw and neck muscles to move a massive traditional microscope head in an unnatural and at times awkward and painful way. Additionally the surgeon's head must align to the microscope at all times; this is difficult and uncomfortable for example when the scope must be tilted by a significant amount to view the surgical site. There is a risk of injury to a surgeon's mouth, face, or eyes caused by the rigid protrusion of the mouth switch structure.

Furthermore, when conventional mouth switch-based controllers are used to unlock the microscope head (e.g., render the microscope as "unconstrained"), the unlocking often causes the surgeon to "lose their place" because the unlocked (e.g., unconstrained) microscope often drifts off the surgical site while the surgeon attempts to move it. This phenomenon results in time-wasting complete repositioning of the microscope each time the microscope is unlocked. Additionally, when the microscope head and control arm are out of balance in any way, the user (e.g., surgeon) may be forced to overcome that mass imbalance with their jaw and neck muscles on every microscope move, adding to the inconvenience and injury risks associated with conventional mouth switch-based controllers.

Various embodiments of the present disclosure address one or more of these shortcomings.

SUMMARY

The present disclosure provides new and innovative systems and methods for controlling a surgical system (e.g., a surgical visualization system and/or an integrated surgical navigation and visualization system) using a hands-free (e.g., actuated using the mouth, nose, or other part of the face or by breath) controller. In an example, a system includes: a microscope camera associated with the surgical system; a controller of the microscope camera; a processor; and a memory storing instructions for the processor. The controller may be separate from the microscope camera, and may comprise a joystick and a pressure detector. The joystick in some embodiments comprises a tube to facilitate air flow. The pressure detector is configured to detect pressure in the tube. In some aspects, the processor may be configured to: receive a movement input based on a movement of the joystick along a Cartesian direction (e.g., via a surgeon's mouth); detect, via the pressure detector, a negative pressure in the joystick caused by a sipping of air from the tube (e.g., by a surgeon); and cause a corresponding movement of the microscope camera along the Cartesian direction. Also or alternatively, the processor may be configured to: receive, via the controller, a second movement input based on a second movement of the joystick along a second Cartesian direction (e.g., via a surgeon's mouth); detect, via the pressure detector, a positive pressure in the joystick, based on a puffing of air into the tube (e.g., by a surgeon); and cause a corresponding second movement of the microscope camera along the second Cartesian direction and a pivot of the microscope camera about a focal point at a destination of the corresponding second movement.

In some embodiments, the processor may detect, via the pressure detector, a double negative pressure in the joystick caused by a double sipping of air from the tube (e.g., by a surgeon). The detection of the double negative pressure may cause the controller to deactivate a sip/puff mode. In some aspects, deactivating the sip/puff mode causes the controller to ignore any X-component of any received movement inputs. Also or alternatively, an activated sip/puff mode causes the controller to perform commands after detecting positive pressure in the joystick (or after detecting negative pressure that is not a double negative pressure in the joystick).

In some embodiments, after the sip/puff mode is deactivated, the processor may be configured to: receive another (e.g., third) movement input based on another (e.g., third) movement of the joystick of the controller along another (e.g., third) Cartesian direction. It is contemplated that the said another movement along the said another Cartesian direction includes at least a Y-axis component (if not also a non-zero X-axis component). The processor may determine a scalar and a direction of the Y-axis component. Furthermore, the processor may be configured to cause a third movement of the microscope camera along a Z-axis. A distance of the third movement of the microscope camera may be proportional to the scalar of the Y-axis component. A direction along the Z-axis may correspond to the direction of the Y-axis component. For example, the movement of the microscope camera along the Z-axis may move the microscope camera towards or away from a field of view (e.g., to zoom in or zoom out of the field of view). The sip/puff mode may be activated again (e.g., reactivated from a deactivated state) after the detection of another second double negative pressure in the joystick caused by a second double sipping of air from the tube.

In an example, a method for controlling a surgical system (e.g., a surgical visualization system and/or an integrated surgical navigation and visualization system) using a mouth, nose, other facial part, and breath actuated controller is disclosed. The example method includes: receiving, by a processor and via a controller comprising a joystick and a pressure detector, a movement input based on a movement of the joystick along a Cartesian direction, wherein the joystick comprises a tube to facilitate air flow; detecting, by the processor and via the pressure detector, a negative pressure in the joystick caused by a sipping of air from the tube; and causing a corresponding movement of a microscope camera of the surgical visualization system along the Cartesian direction. Also or alternatively, the method includes: receiving, by the processor and via the controller, another (e.g., second) movement input based on another (e.g., a second) movement of the joystick along another (e.g., a second) Cartesian direction; detecting, by the processor and via the pressure detector, a positive pressure in the joystick caused by a puffing of air into the tube; and causing a corresponding second movement of the microscope camera of the surgical visualization system along the second Cartesian direction, and a pivot of the microscope camera about a focal point at a destination of the corresponding second movement.

In another example, a hands-free controller for a surgical visualization system is disclosed. The controller may be configured to enable a surgeon to control microscope six degrees of freedom (6DOF) pose, including mechanical focus. The controller may have a constrained mode that enables the surgeon to control single important parameter only, such as focus, while not affecting other parameters. The controller may include mode switching to allow large amount of controls. Each mode or "page" of parameters may be controlled by a small amount of physical inputs and one of those inputs switches through modes, and robotic control to enable the controller to be completely separated from microscope. The controller does not interfere with function of traditional controls. In some aspects, a movement limit per input prevents unintended larger microscope moves and protects patient.

In another example, a non-transitory computer-readable medium is disclosed for use on a computer system containing computer-executable programming instructions for performing one or more methods described herein.

In another example the hands free controller comprises multiple actuator components such as multiple joysticks each dedicated to a function of microscope control and the activation method is a proximity detector mounted on the user's 3D glasses (worn in use of the digital surgical microscope.) The dedicated actuator components mitigate the need to switch control modes. Additionally such an activation method and joystick control facilitates use of the hands free controller through a surgical drape and surgical mask.

In another example, a system for controlling a surgical system using a multi-component controller that is hands-free is disclosed. The system may include a microscope camera (e.g., associated with the surgical visualization system or the integrated surgical navigation and visualization system), the multi-component controller of the microscope camera, a processor, and a memory. The multi-component controller may be separate (e.g., physically and/r functionally) from the microscope camera (e.g., to allow controls on the microscope camera to also independently control the microscope camera). The multi-component controller may include a plurality of joysticks (including at least a first joystick) and a keyed proximity detector. The keyed proximity sensor may be configured to activate the multi-component controller after detecting a detector key associated with a user. The memory may store instructions that, when executed by the processor, can cause the processor to perform one or more steps or processes. For example, the processor may be configured to: detect, based on the detector key being within a predetermined distance to the keyed proximity detector, a presence of the user; activate the multi-component controller to receive user input; receive a movement input based on a movement of the first joystick along a Cartesian direction; and cause a corresponding movement of the microscope camera along the Cartesian direction.

In some embodiments, each joystick is configured to perform a unique function of the microscope camera. For example, the plurality of joysticks may include the first joystick configured to cause linear movements of the microscope camera; a second joystick configured to cause rotational movements of the microscope camera along a pivot; a third joystick configured to cause the microscope camera to increase or decrease a focus; and a fourth joystick configured to cause the microscope camera to zoom in or zoom out. In some aspects, each of the plurality of joysticks can be reprogrammed or configured to be programmable for performing another function of the microscope camera (e.g., adjusting lighting intensity, fluorescence controls, and/or image processing modes). The plurality of joysticks may be spaced apart and arranged horizontally to avoid interference with each other while being actuated. The plurality of joysticks may be configured for surgical draping. Furthermore, each joystick can be configured to be actuated by one or more areas of a face of the user. For example, one or more of the plurality of joysticks is configured to have a facial contour-conforming shape (e.g., a rounded cap).

In some embodiments, the keyed proximity detector comprises a radiofrequency identification (RFID) detector, and wherein the detector key comprises a short range RFID antenna. Also or alternatively, the keyed proximity detector comprises a QR scanner, and wherein the detector key comprises a QR code. In some aspects, the detector key may be associated with the user (e.g., a surgeon) by being attached to a 3D glass worn by the user, or being placed or affixed to a nose bridge of the user.

In some embodiments, the processor may be further configured to: receive a second movement input based on a movement of a second joystick of the plurality of joysticks along a Cartesian direction; and cause a corresponding rotational movement of the microscope camera along a pivot based on a current position of the microscope camera. Also or alternatively, the processor may be further configured to: detect, based on the detector key no longer being within the predetermined distance to the keyed proximity detector, an absence of the user; deactivate the multi-component controller; receive an unintended movement input based on an unintended movement of one of the plurality of joysticks; and ignore the unintended movement input based on the deactivation of the multi-component controller.

In yet another example, a method for controlling a surgical system using a multi-component controller that is hands-free is disclosed. The method may include detecting, by a processor, based on a detector key being within a predetermined distance to a keyed proximity detector associated with the multi-component controller, a presence of a user of the multi-component controller. The detector key (e.g., an RFID antenna, a QR code, etc.) may be associated with the user (e.g., a surgeon). The multi-component controller may include the keyed proximity detector (e.g., an RFID detector or scanner, a camera, etc.) and a plurality of joysticks including at least a first joystick. Responsive to the detection, the multi-component controller may be activated to receive user input. For example, the processor may receive, via the multi-component controller, a movement input based on a movement of the first joystick along a Cartesian direction; and cause a corresponding movement of a microscope camera along the Cartesian direction, wherein the multi-component controller is separate from the microscope camera. Also or alternatively, the processor may receive a second movement input based on a movement of a second joystick of the plurality of joysticks along a Cartesian direction; and may cause a corresponding rotational movement of the microscope camera along a pivot based on a current position of the microscope camera.

The method may further include: detecting, based on the detector key no longer being within the predetermined distance to the keyed proximity detector, an absence of the user; deactivating the multi-component controller; receiving an unintended movement input based on an unintended movement of one of the plurality of joysticks; and ignoring the unintended movement input based on the deactivation of the multi-component controller.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Apparatuses, methods, and systems are disclosed that provide a hands-free surgical microscope controller. The controller may be actuated using the mouth, nose, breath, or tongue, or other parts of the face such as the area above the chin below the mouth and may provide for a hands-free operation. The hands-free aspect of the controller saves time associated with using the hands to perform various functions (e.g., repositioning the scope to better view the surgical site moving or otherwise controlling the scope to re-focus, change magnification (zoom), etc.). Furthermore, the hands-free controller is more convenient and effective than conventional controllers and poses less injury risks. In some embodiments, the hands-free controller may have multiple components (e.g., multiple joysticks) and may rely on a keyed proximity sensor to be activated, along a user to actuate any one of its joysticks using any parts of the face of the user. As used herein, an activation may refer to providing the hands-free controller to respond to various inputs corresponding to movement or other physical contact of any of the hands-free controller's joysticks or buttons (e.g., by causing corresponding movement and other functions on a microscope camera). An actuation may refer to the movement or other physical contact of the hands-free controller that causes the hands-free controller to command the microscope camera to perform various functions described herein.

Figure 1:
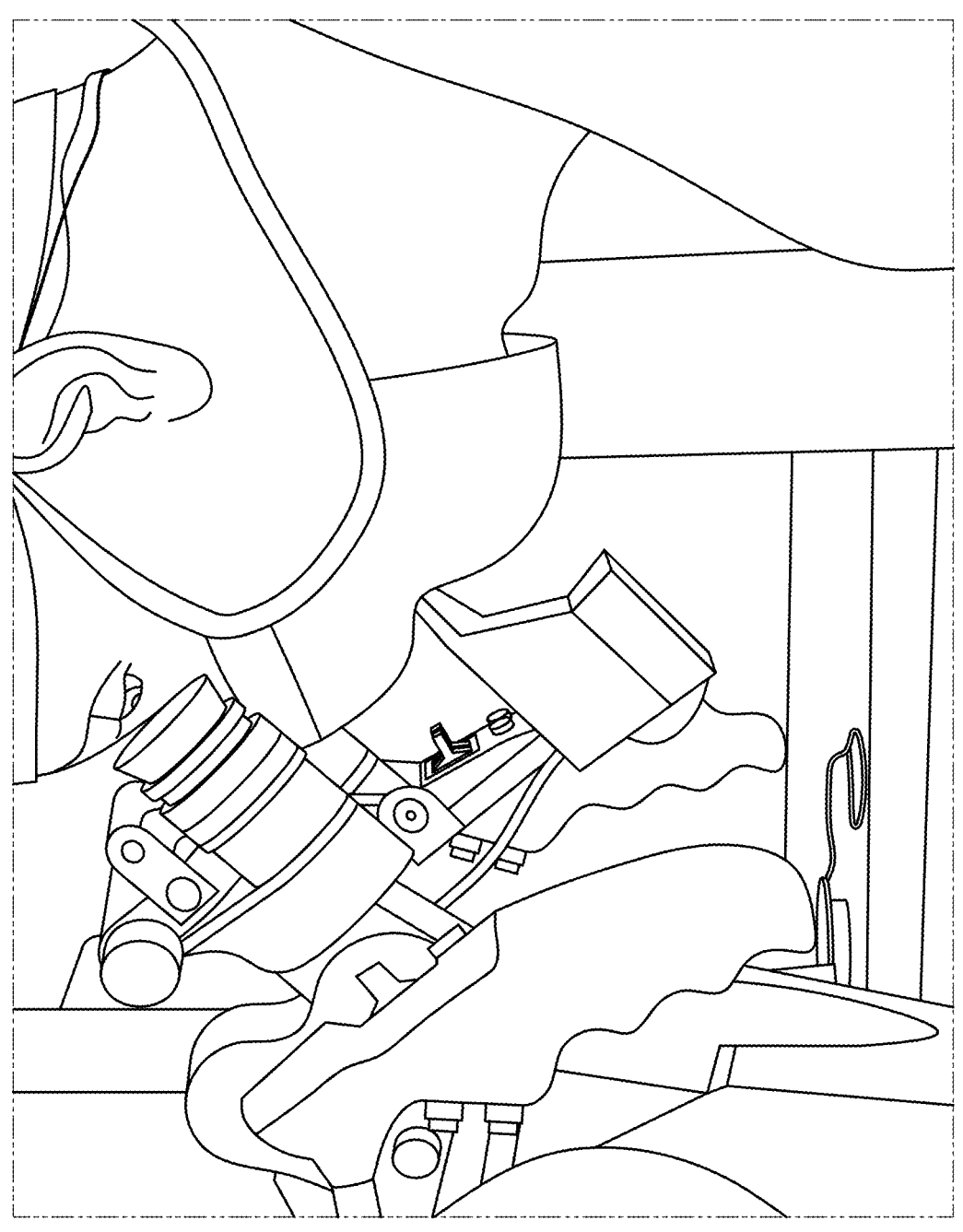
FIG. 1 shows a surgeon using his hands to adjust a conventional mouthpiece in a conventional digital surgical microscope controller.
Figure 2A:
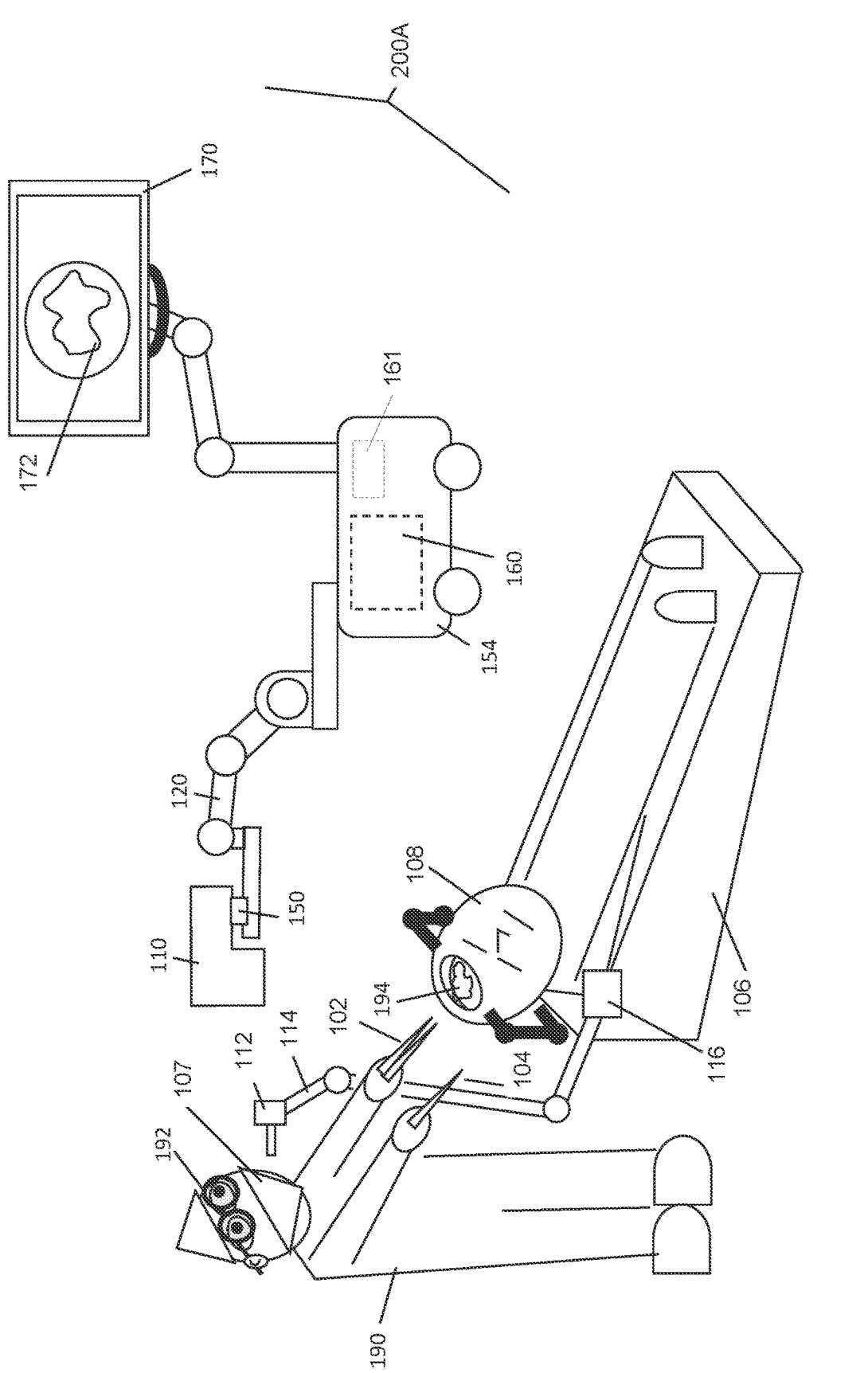
FIG. 2A shows an example hands-free surgical microscope controller applied to a surgical visualization system, according to an example embodiment in the present disclosure.

FIG. 2A shows a surgical visualization system 200A, according to an example embodiment in the present disclosure. The surgical visualization system 200A includes a stereoscopic camera 110, a robotic arm 120, a force-torque sensor 150, a cart 154, an embedded processing unit (EPU) 160, a memory 161, and a display monitor 170 showing an optionally magnified view of surgical site on 3D stereoscopic display 172. FIG. 2A also shows a surgeon 190, three-dimensional glasses 192 for viewing stereoscopic images on the display monitor 170, a surgical tool 102, another surgical tool 104, a surgical bed 106, a surgical mask 107, and a patient 108.

The stereoscopic camera 110 is mounted on the robotic arm 120 and removes the requirement that the surgeon 190 be physically constrained to the microscope pose by having to look through oculars attached to the scope as in traditional primarily optical microscopes. Instead, the surgeon views the surgical field 194 on a 3D stereoscope display 170 while standing or sitting in a pose completely freed from the pose of the microscope.

For head-based control, the surgical visualization system 200A includes a mouth-, nose-, and breath-, actuated controller 112, a controller articulated mounting arm 114, and a bed mount base for controller articulated mounting arm 116. The hands-free surgical microscope controller 112 (also referred to herein as "controller" 112) is mounted on the articulated arm 114. The articulated arm can in turn be mounted on bed mount base for articulated mounting arm 116. The bed mount base mounts in some embodiments to the patient bed 106 and in other embodiments to some nearby convenient physical structure such as its own stand.

Figure 2B:
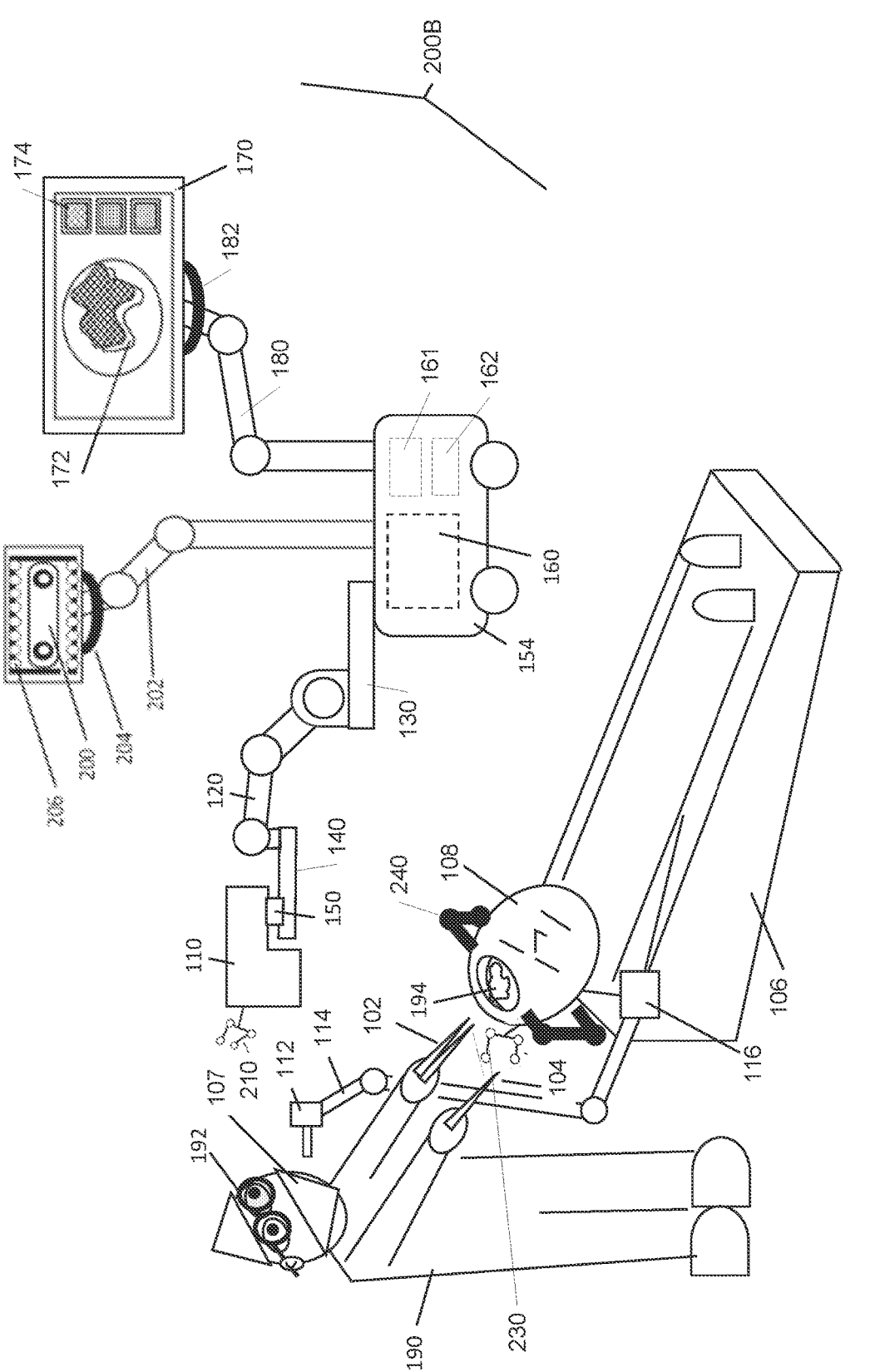
FIG. 2B is a diagram showing an example hands-free surgical microscope controller applied to an integrated surgical navigation and visualization system, according to an example embodiment of the present disclosure.

FIG. 2B is a diagram showing an example hands-free surgical microscope controller applied to an integrated surgical navigation and visualization system 200B, according to an example embodiment of the present disclosure. As shown in FIG. 2B, the integrated surgical navigation and visualization system 200B may include a digital surgical microscope (DSM) head 110 mounted on a robotic arm 120. To enhance robotic arm reach, the robotic arm 120 may be mounted on an extension platform ("diving board") 130. To extend the range of orientations in which the integrated surgical navigation and visualization system can be used, the DSM head 110 can be mounted on a "universal" coupler 140, which may provide one or more additional degrees of freedom beyond the end of the robotic arm.

A force-torque sensor 150 may be incorporated into the robotic arm-DSM head combination. The force-torque sensor 150 may allow users to pose the DSM head at will using physical actions (e.g., as legacy microscopes). For example, the user can physically grab some part or parts of the DSM head or handles attached or otherwise coupled to the robotic arm, and can direct the head toward the desired pose. The force-torque sensor 150 can detect the physical input. A software control module can convert the force-torque sensor's output into an intended change in pose. The same or an additional control module can convert such user intent into a set of robot pose changes that can be streamed to the robot to effect the changes.

However, as described herein, the use of the force/torque sensor 150 to control the DSM head 110 (e.g., to adjust the field of view) may be in addition to or may be replaced with the use of the hands-free (e.g., mouth, breath, nose, other facial part or tongue-actuated) controller 112.

The integrated surgical navigation and visualization system 200B may further include a cart 154. The cart 154 can provide a support structure for the robotic arm and diving board. Furthermore, the cart 154 may include an embedded processing unit (EPU) 160, a memory 161, and a power management unit with uninterruptible power supply (PMU/UPS) 162. The EPU 160 can communicate with the DSM head and/or the hands-free controller 112, sending commands and receiving command responses (e.g., image data and status data from the DSM head, and commands from the hands-free controller 112). Also or alternatively, the EPU 160 may perform one or more steps, methods, or processes described herein using computer-executable or machinereadable instructions stored in the memory 161. The PMU/UPS 162 can manage power for the integrated surgical navigation and visualization system 200B. The uninterruptible power supply (UPS) 162 can provide the user with the option to unplug the cart for a short time to reposition if needed. The PMU/UPS 162 can also provide the surgeon with an option to have a short time to transition to backup equipment should the hospital power fail.

Imagery can be captured by the digital surgical microscope's optics and image sensor electronics (not shown) and commands can be registered from the hands-free controller 112. The image data and command signals can be sent to the EPU, processed, and then sent to the three-dimensional (3D) stereoscopic display 170. The 3D stereoscopic display 170 may be mounted on an articulated display mounting arm 180. Its pose may be controlled by display pose adjustment handle 182 e.g., to allow the user to pose the display for optimal viewing quality and comfort. Also or alternatively, the pose may be controlled via the hands-free controller 112. In some embodiments, the localizer may also be equipped with a camera to capture a field of view of the surgical site. Furthermore, the display 170 showing image data captured by the digital surgical microscope may also show (e.g., as an overlay) a field of view of the localizer.

The surgeon 190 may wear 3D glasses 192 to view the 3D stereoscopic display. The 3D glasses 192 may provide the surgeon to view a 3D stereoscopic view of surgical site 194. Zoom and focus optics in the digital surgical microscope can be controlled by the user, and can provide 3D stereoscopic focused views of the surgical site over a range of working distances (e.g., 200 millimeters (mm)-450 mm) and magnifications (e.g., 3×-11×). In some embodiments, the 3D glasses are passive wherein the polarizing film on each respective lens of the glasses left and right are respective conjugates to polarizing film applied to every other line on the display (e.g. the left glasses lens passes the even-numbered lines of the display and block the odd-numbered lines, and vice-versa). In some embodiments the 3D glasses are active shutter types synchronized to the display such that the left eye passes e.g. every other time-sequential frame shown on the display and blocks the remainder and the right eye performs the complement. In some embodiments, the 3D display may be "glasses-free" and may provide 3D display to the user without need for 3D glasses.

As used herein, "working distance" and "focus" may be used interchangeably. Furthermore, the user interface of the integrated surgical navigation and visualization system 200B may refer to working distance as the variable parameter. When a change is made to the desired working distance, the optics move such that the focus distance changes. Thus, the distance between the microscope and the focus surface may change, and that distance can be generally considered to be the working distance.

The navigation localizer 200 (also referred to herein as "localizer") may be mounted on the articulated localizer mounting arm 202. The navigation localizer 200 may be user-poseable by localizer pose adjustment handle 204.

A navigation-trackable patient reference target 230 can be mounted rigidly to a patient clamp (e.g. a "Mayfield" clamp) 240. The patient clamp 240 may be mounted near surgical bed 106 where the patient 108 resides. The patient clamp 240 may avoid areas of the patient's anatomy to move in relation to the patient reference array.

The digital surgical microscope may be rendered to be compatible with (e.g., by being rendered trackable by) the localizer with the addition of the DSM navigation target (e.g., "shellmet," as derived from "shell" and "helmet.")

210. Various styles of navigation targets can be used with the system such as the retro-reflective spheres shown schematically in the Figure or image-based corner targets described elsewhere in this document.

In some embodiments, the localizer 200 may also be equipped with a camera to capture a field of view of the surgical site. Furthermore, the display 170 showing image data captured by the digital surgical microscope may also show (e.g., as an overlay) a field of view of the localizer 200.

The localizer 200 may detect the pose in some reference frame of compatible devices (i.e. trackable devices, navigation targets) in its viewing space. The localizer 200 may supply this information to the EPU responsive to requests for such information in a quasi-real-time fashion (e.g., 15 times per second in a "polling" method) or at a constant rate even without requires (a "broadcast" method). Typically, the reference frame in which the poses are reported may be that of the localizer. In some implementations, however, pre-calculations may be performed in order to report the poses from a different reference frame.

Relevant rigid patient anatomy such as the skull may be mounted to or accessible via, clamp 240. Systems and methods described herein may guide the user through a patient anatomy registration procedure, as part of the preparation workflow. This registration procedure can determine the pose of the patient data relative to the navigation target affixed rigidly either directly or indirectly to the relevant patient anatomy.

Figure 3:
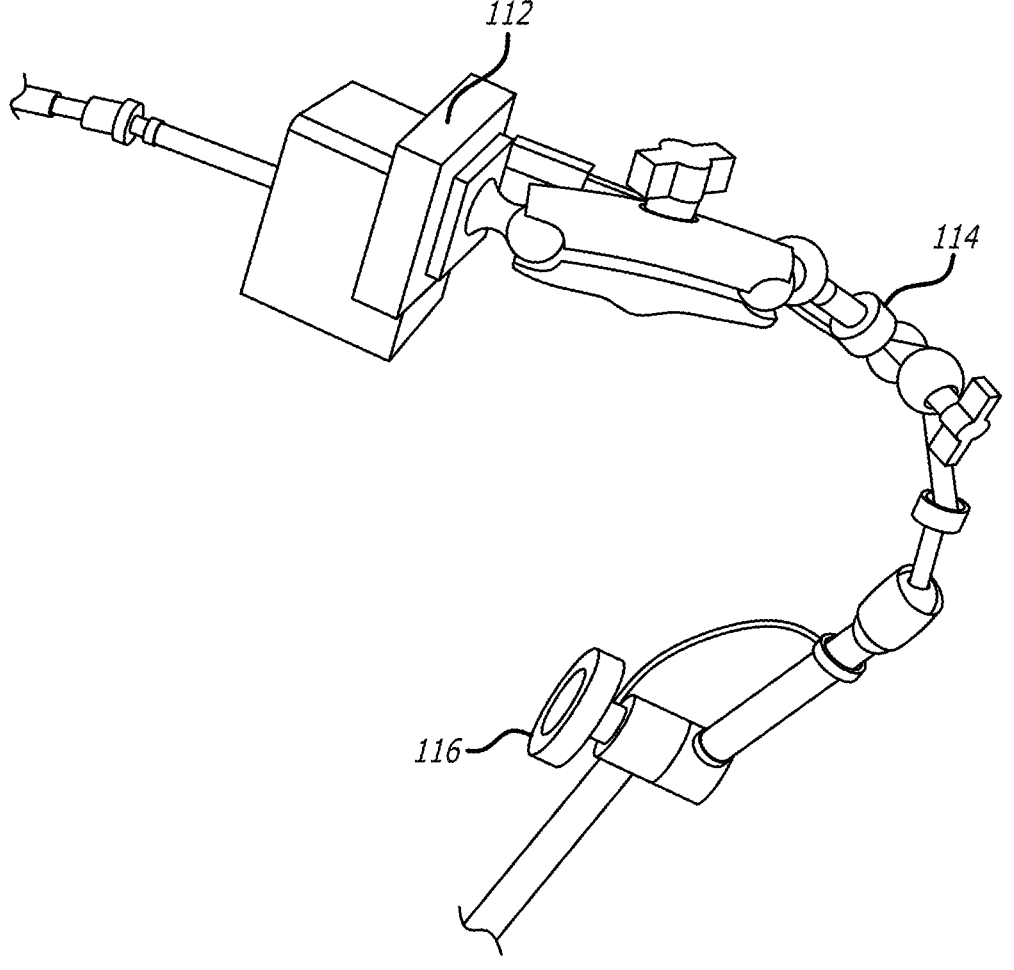
FIG. 3 is a diagram of a hands-free surgical microscope controller, which is mounted on an articulated arm, according to an example embodiment of the present disclosure.

FIG. 3 is a diagram of the hands-free digital surgical microscope controller 112, which is mounted on the articulated arm 114, according to an example embodiment of the present disclosure. As shown, the controller 112 can be positioned "nearby" the surgeon without being obtrusively in the surgeon's face for the whole procedure.

The primary control of the controller 112 is a joystick with the stick containing a drinking straw-like channel with an air pressure sensor at the distal end. The joystick is actuated by the mouth or nose and provides two-dimensional input. In some embodiments, this is used directly as input to move the microscope in onscreen X and Y linear directions. An air pressure sensor enables additional parameter input controlled by air pressure in the user's mouth relative to the joystick air channel. The air pressure sensor may be generate command signals based on sensed physical input, including but not limited to: a negative pressure ("sip"); a positive pressure ("puff"); and no pressure ("neutral" or "no pressure"). In some embodiments, advanced signals or commands based on sensed physical inputs may include varying control parameter value(s) as a function of the value of such pressure provided. In some aspects, additional auxiliary channel-only (no joystick) inputs may provide further control parameter input.

Figure 4:
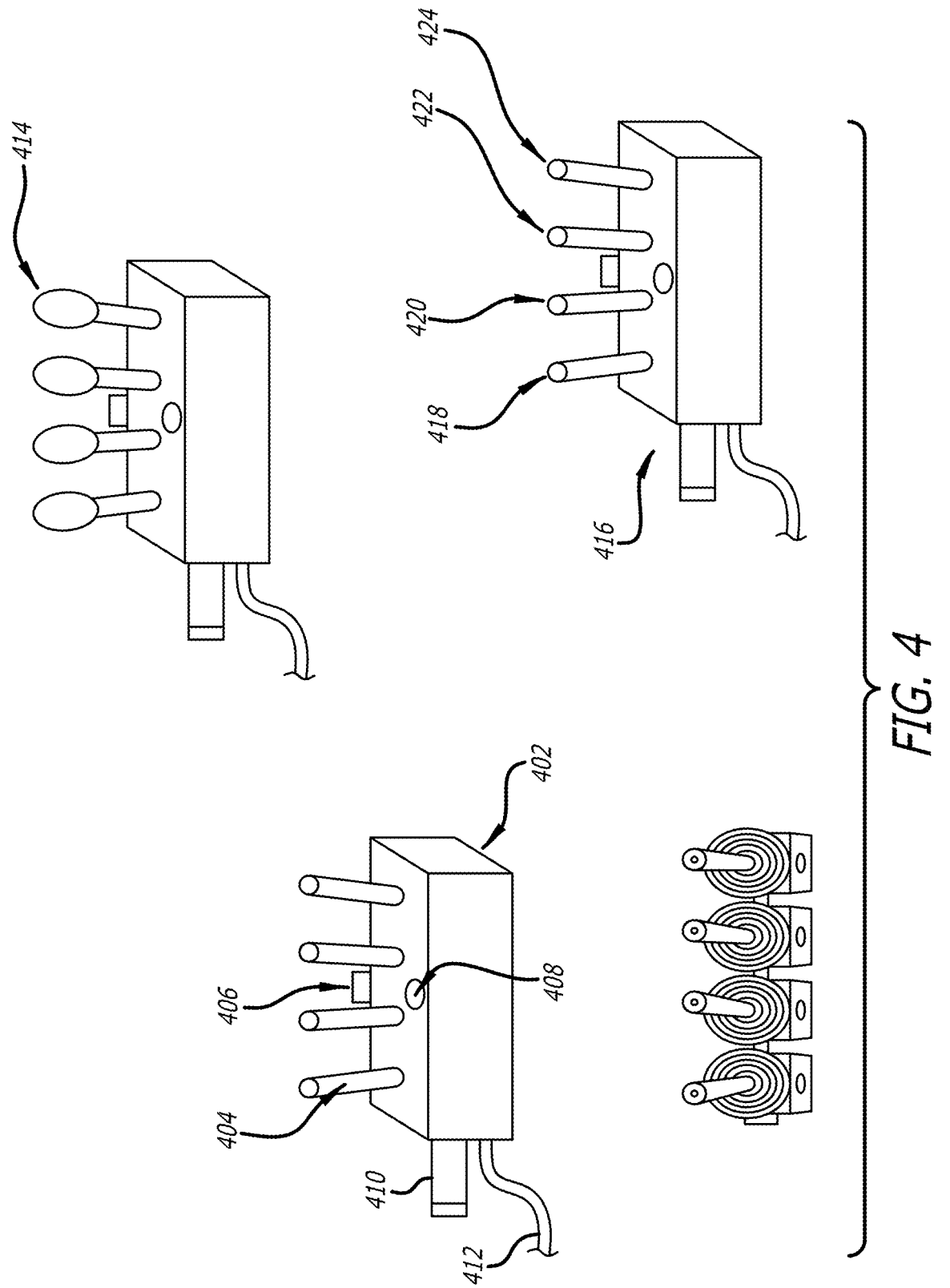
FIG. 4 is a diagram of multi-component hands-free surgical microscope controllers, according to an example embodiment of the present disclosure.

FIG. 4 is a diagram of multi-component hands-free digital surgical microscope controllers (also referred to herein as "multi-component controllers"), according to an example embodiment of the present disclosure. A multi-component controller may have multiple actuators or joysticks (e.g., as in the four joysticks 404 seen in multi-component controller 402). The multi-component controller may remove the reliance on the mouth and breath, and may ensures that usage through a surgical drape and surgical mask is easy, intuitive and comfortable, while also providing multiple functions simultaneously without the need to switch modes. Furthermore, a multi-component controller may be activated via a keyed proximity detector 406. For example, the keyed proximity detector 406 may comprise an RFID detector chip on the body of the controller that is configured to detect the proximity of the surgeon based on a short-range RFID antenna attached to the bridge of surgeon's nose or to the surgeon's 3D glasses. In some aspects, the controller may be activated only when the RFID chip is within a certain range (e.g., within 100 mm) of the RFID antenna. Before detection, the controller may be inactive to avoid reacting to unexpected and unwanted movements of the joystick (e.g., due to foreign objects hitting it or due to the controller falling to the floor unexpectedly). In one embodiment, the controller activation process may rely on a small camera on the controller device (e.g., in addition to or as an alternative to the RFID detector chip) and a QR code mounted on the 3D glasses (e.g., in addition to or as an alternative to the RFID antenna). Any of the above devices within the multi-component controller for proximity detection to activate or deactivate the multi-component controller may be referred to herein as a "keyed proximity detector" where the proximity is confirmed in the presence of a pre-determined object type (e.g., an RFID antenna with an RFID detector as described or else a QR code on the 3D glasses). Furthermore, any of the above devices associated with the user (e.g., by being attached to an accessory (e.g., 3D glasses) or a person of the user) that is detected by the keyed proximity detector may be referred to herein as "detector key."

In some aspects, the multi-component controller may include a microphone 408 for voice control to complement the joystick control. A mechanical mount 410 may connect the controller to a bed rail or an arm of the bed rail. The multi-component controller may rely on wiring 412 for power connection or for communication with the surgical visualization system 200A and/or the integrated surgical navigation and visualization system 200B. Also or alternatively, the multi-component controller may rely on wireless communication or battery power.

In some embodiments, the joysticks of a multi-component controller may have rounded caps for smoother "rolling" usage, or otherwise have facial contour-conforming shapes. For example, the rounded caps can allow a user to "roll" over the rounded caps (e.g., using their mouth and/or lips area, or the area above the chin below the lips) to control a given function.

In some embodiments, each joystick of a multi-component controller may be used for a different function. For example, as shown in multi-component controller 416 of FIG. 4: joystick 418 may be used to cause a DSM camera 110 to undergo a linear X-Y movement; joystick 420 may be used to cause a DSM camera 110 to rotate (e.g., pivot) by causing X-Y movement of the joystick 420; joystick 422 may be used to provide focus; and joystick 424 may be able to cause the DSM head to zoom in or zoom out (e.g., by causing the DSM head 110 to move along the Z-axis with respect to the surgical site). Each joystick may be arranged horizontally with enough spacing to avoid interference with each other.

In some embodiments, the multi-component controller allows many parts of the face to control the controller, and not just the mouth and nose. For example, the chin or the area above the chin may be used to control some of joystick(s) on the multi-component controller, while some users might prefer using the lips and surrounding areas, or the nose and surrounding areas. In some aspects, the multiple-component controllers may remove the use of breath (e.g., double sipping) to change modes.

Figure 5:
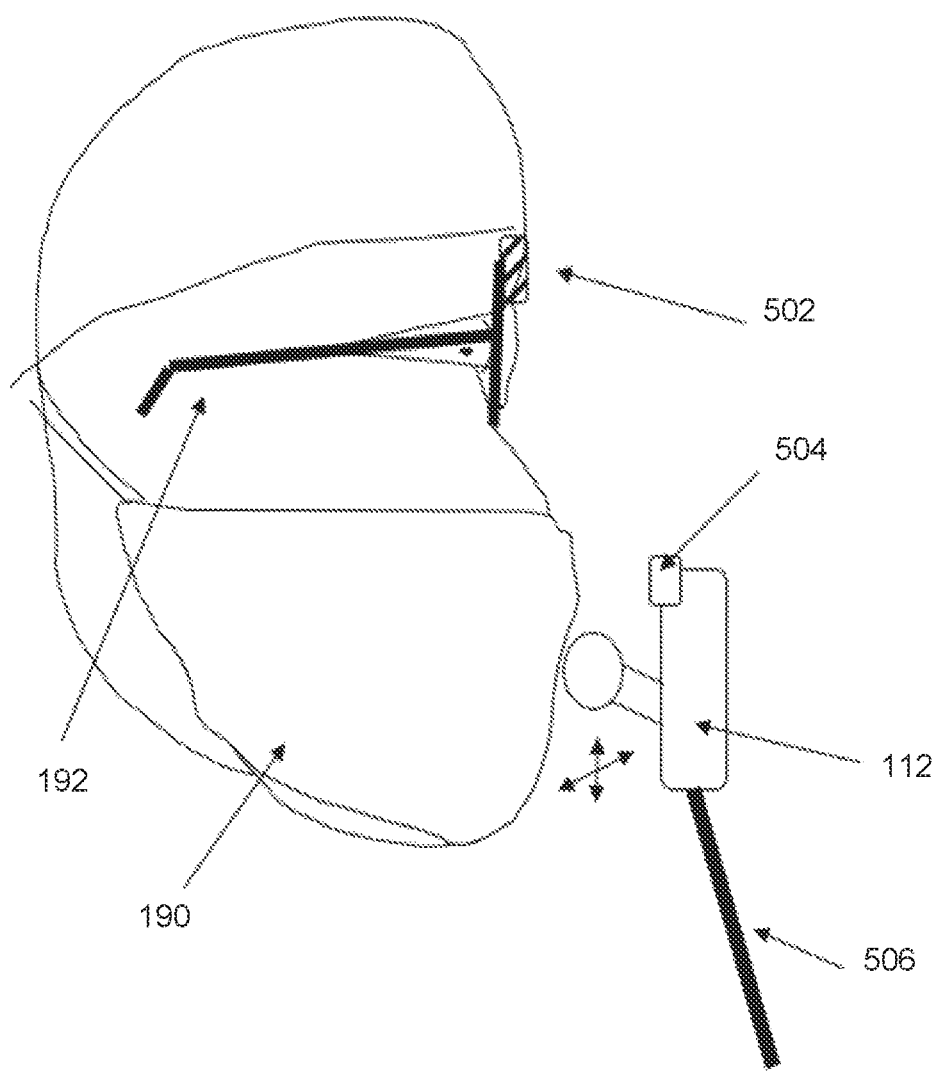
FIG. 5 is a diagram of surgeon using a hands-free surgical microscope controller, according to an example embodiment of the present disclosure.

FIG. 5 is a diagram of surgeon using a hands free (e.g., mouth-, nose-, and breath-actuated) digital surgical microscope controller (also referred to herein as "controller"), according to an example embodiment of the present disclosure. As shown in FIG. 5, the surgeon 190 may wear 3D glasses 192 to conveniently view a display 170 distant from the surgeon (e.g., that shows the field of view of the DSM camera 110). The 3D glasses 192 and/or the distant display 170 may thus obviate or alleviate the burden typically required for surgeons of closely attending to a microscope or other viewing device while also inconveniently controlling the microscope through a mouthpiece blocking the surgeon's face. In some embodiments, the surgeon may be able to activate and/or access the controller 112 through a proximity key 502 (e.g., mounted on the 3D glasses 192 and/or on the surgeon's person). The proximity key 502 may be able to cause a proximity key detector 504, located on the controller 112, to detect the presence of the surgeon 190. The detection may cause the controller 112 to activate, allowing the surgeon 190 to control the surgical visualization system 200A or the integrated surgical navigation and visualization system 200B hands-free (e.g., via mouth, nose, breath, and/or tongue). The controller 112 may be connected or attached to a bed rail or to the surgeon's person via a mount 506.

Figure 6:
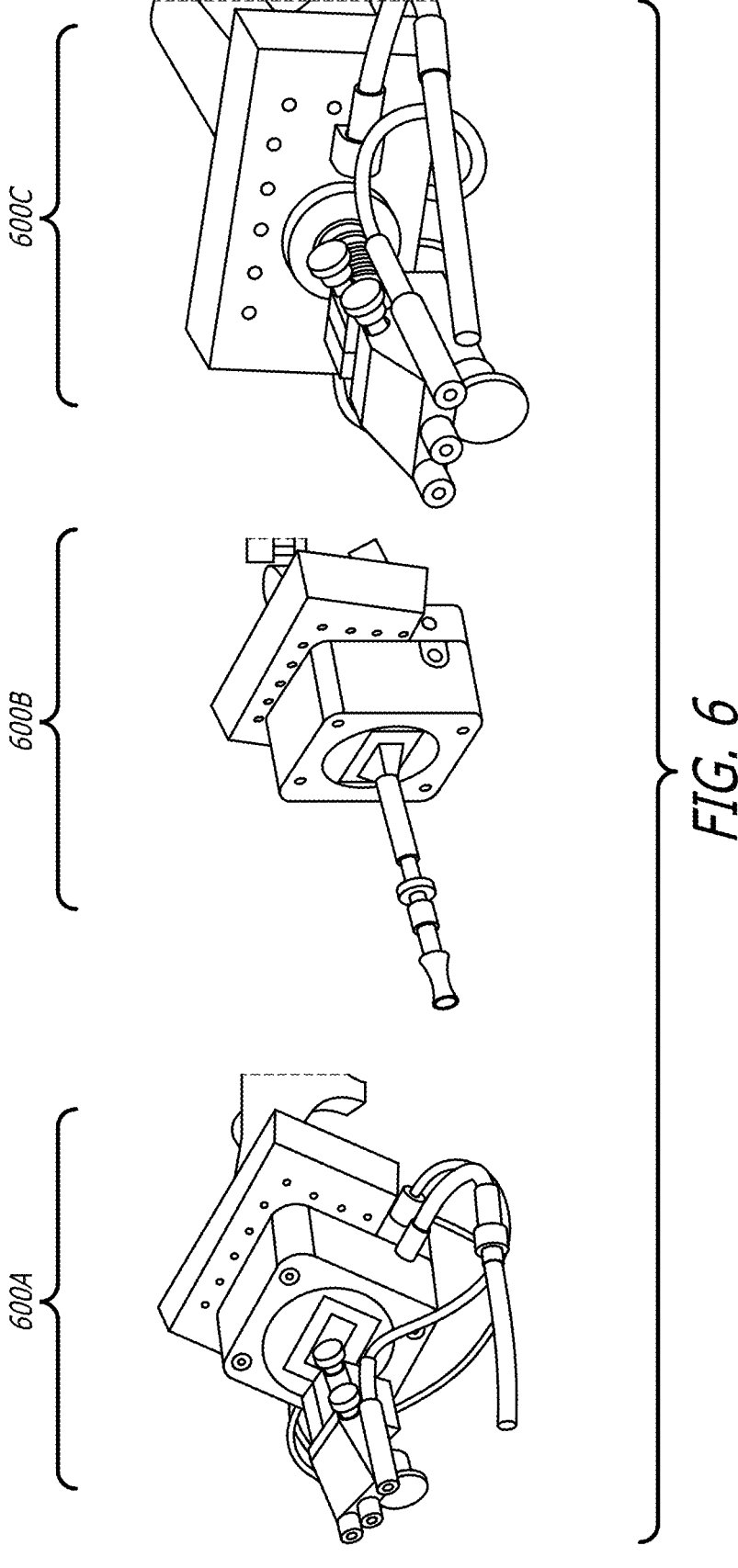
FIG. 6 is an illustration of three examples of the hands-free controllers used in FIGS. 2A and 2B, according to an example embodiment of the present disclosure.

FIG. 6 is an illustration of three examples of the hands-free digital surgical microscope controllers (also referred to herein as "controller") used in FIGS. 2A and 2B, according to an example embodiment of the present disclosure. As shown in FIG. 6, the three controllers 600A-600C differ in their primary controls and/or joysticks. In some aspects, the controller (e.g., controllers 600A-600C of FIG. 6 or controller 112 of FIGS. 2A-2B) may be mechanically independent from the microscope head and may be widely adjustable for optimum surgeon pose. Furthermore, the controllers (e.g., controllers 600A-600C of FIG. 6 or controller 112 of FIGS. 2A-2B) may enable optimal ergonomics of camera 110 to be maintained and may use much less force and torque required to operate compared to traditional microscope-bound mouth controller. Even further, the controllers (e.g., controllers 600A-600C of FIG. 6 or controller 112 of FIGS. 2A-2B) may be operable by other non-hand parts of the surgeon, such as the nose, the tongue and the breath, may use deterministic controls with minimal lag, and may have mode switching to allow large amount of controls. The controllers (e.g., controllers 600A-600C of FIG. 6 or controller 112 of FIGS. 2A-2B) can be much less intrusive than traditional optical microscope mouth controllers. In some embodiments, the controllers (e.g., controllers 600A-600C of FIG. 6 or controller 112 of FIGS. 2A-2B) work independently from existing microscope inputs, such as the force-torque sensor 150, and may not interfere with the existing microscope inputs.

Figure 7:
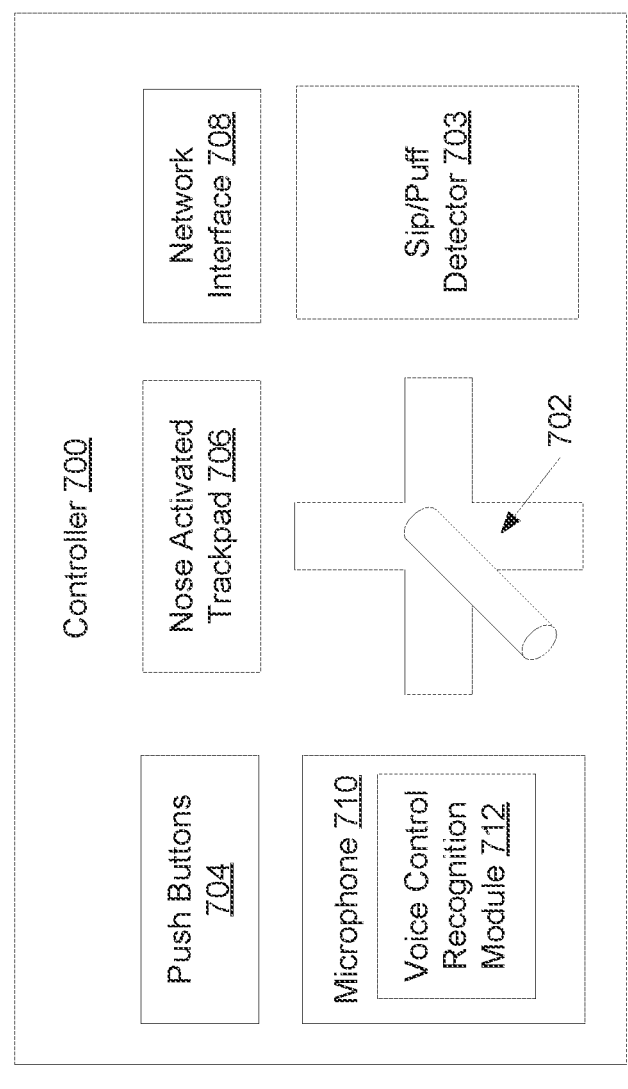
FIG. 7 is a component diagram of an example hands-free surgical microscope controller, according to an example embodiment of the present disclosure.

FIG. 7 is a component diagram of an example hands-free digital surgical microscope controller (referred to herein as "controller"), according to an example embodiment of the present disclosure. As shown in FIG. 7, the controller 700 (e.g., one of controllers 112, 600A-600C, etc.) may comprise a joystick 702 that can move along Cartesian coordinates (e.g., an XY joystick, XYZ joystick, etc.). For example, a surgeon may use their mouth to move the joystick along a Cartesian direction. In some aspects, the movement may be accompanied by a sip or a puff through the joystick, which may comprise a tube to allow air flow associated with the sip or puff. The controller 700 may thus include a sip/puff detector, which may comprise a positive and negative pressure sensor to detect the sip and puff, respectively. It is contemplated that additional sip/puff pressure sensors (e.g., of an N number) may be present for additional information about the sip or puff (e.g., whether there is a double sip or double puff to cause a change in sip-puff mode, as will be discussed herein). In some aspects, the controller 700 may include additional joysticks present (e.g., as previously discussed in relation to FIG. 4) of an N number. Also or alternatively, the controller may include a six degrees of freedom (6DOF) controller (e.g., Space Navigation style).

The controller 700 may further include a nose activated trackpad 706, which may allow the surgeon to conveniently activate the controller using the surgeon's nose. The controller 700 may further include push buttons 704 for additional functionalities (e.g., focus, brightness, contrast, etc.). In some embodiments, the functions for dedicated controls (e.g., push buttons 704 and joystick 702) may be programmable. For example, a default set of functions (e.g., linear XY movement input, rotational (e.g., pivot) XY movement input, focus, zoom, etc.) can be expandable to include most or all of the functions used during typical surgical procedures (e.g., including but not limited to lighting intensity, fluorescence controls and image processing modes). In some embodiments, the controller 700 may include an attached microphone 710 to allow the surgeon to control the microscope and/or integrated surgical visualization and navigation system using oral commands. For example, the microphone 710 may include a voice control recognition module 712 that may comprise a software, program, or instruction that uses natural language processing of the surgeon's speech to determine and transmit commands (e.g., to the EPU 160). In some aspects, other dedicated or mode-based controls can be added or programmed into the controller, based on the surgeon's appetite for complexity. Furthermore, the controller 700 may include a network interface 708 to facilitate wired or wireless operation and communication with other components of the surgical visualization system 200A or integrated surgical navigation and visualization system 200B.

The controller 700 may include appropriate safeguards for hygiene and sterility. For example, the controller 700 may be configured for the use of a sterile drape, where needed, and/or the controller 700 may be wrapped or partially covered by the sterile drape. Furthermore, the controller 700 may use sterile single or low-use mouthpieces for multiple users.

Figure 8:
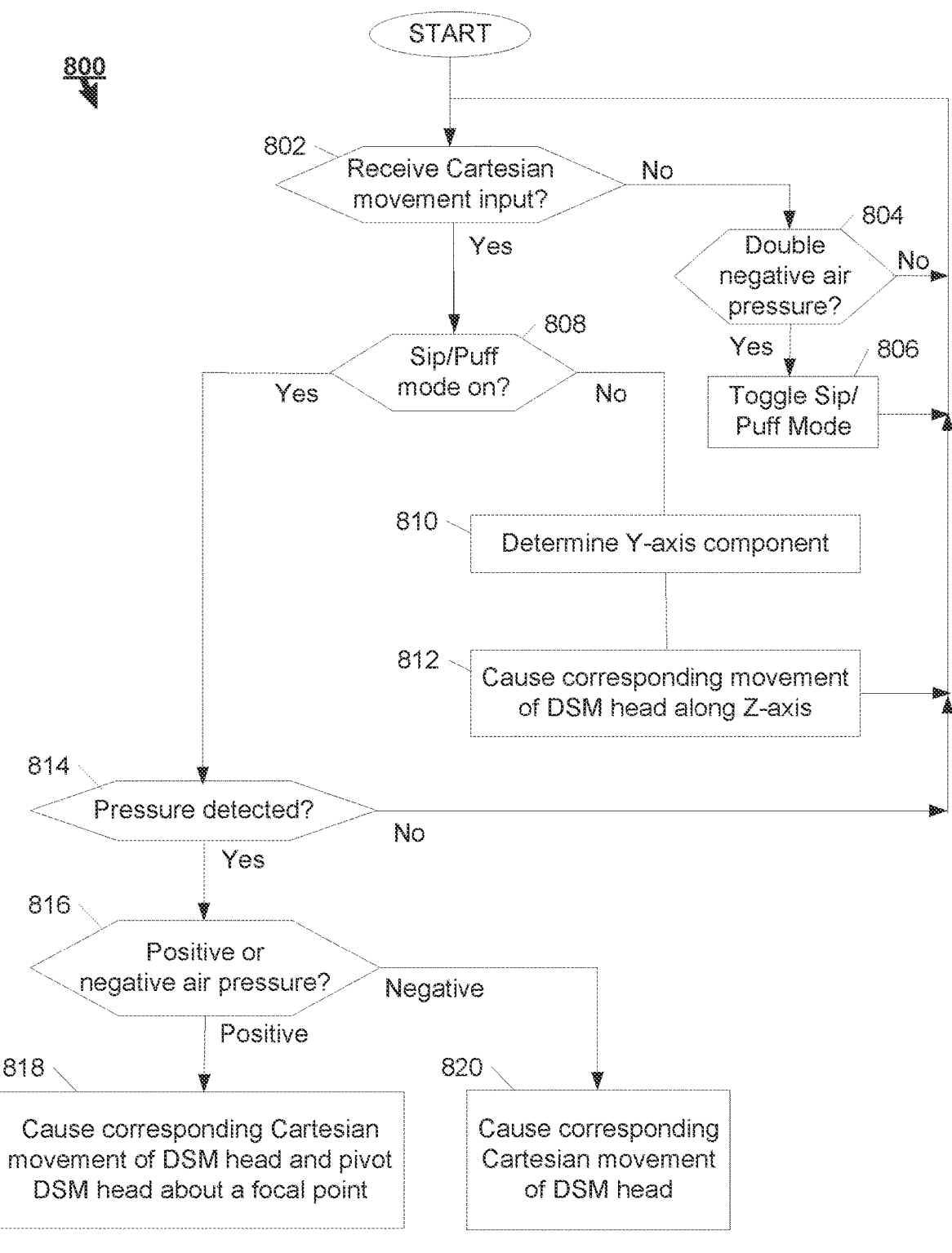
FIG. 8 shows an example process performed by surgical visualization system and/or the integrated surgical navigation and visualization system based on the hands-free (e.g., mouth-, nose-, other facial part-, and breath-actuated) digital surgical microscope controller, according to an example embodiment of the present disclosure.

FIG. 8 shows an example process 800 performed by surgical visualization system and/or the integrated surgical navigation and visualization system based on the hands-free (e.g., mouth-, nose-, and breath-actuated) digital surgical microscope controller (also referred to herein as "controller"), according to an example embodiment of the present disclosure. For example, one or more blocks of process 800 may be performed by the embedded processing unit (EPU) 160 of the surgical visualization system 200A or of the integrated surgical navigation and visualization system 200B. In some aspects, one or more processors of the EPU 160 may perform processes associated with the blocks based on computer-executable or machine-executable instructions stored in the memory 161. Also or alternatively, one or more blocks of process 800 may be performed by a computer processing unit (CPU) associated with a local computing device or associated with a remote server or computing system. For simplicity, "processor" may be used to refer to the performer of one or more blocks of process 800, and may refer to any of the above described processing units.

For example, process 800 may begin with the process determining whether it has received any Cartesian movement input (block 802). For example, if the user moves (e.g., with their moth, nose, tongue, etc.) the joystick 702 in an XY direction, the controller 700/112 may register the movement as a Cartesian movement input. If not, or alternatively, the processor may determine whether it has received any input comprising a double negative air pressure. The double negative air pressure may involve the user (e.g., surgeon) causing two rapid sips (inhalation of air from the joystick) (also referred to herein as a "double sip"). In some embodiments, the double sip may be a mode switch control causing the system to switch on or switch off the sip/puff mode, as will be discussed herein. For example, the sip/puff detector 703 may detect a rapid sequence of negative pressure generation (e.g., based on the period between each negative pressure thrust occurring within a predetermined duration). If there is an input based on double negative air pressure input, the processor may cause the controller to toggle the sip/puff mode (block 806). For example, if the sip/puff mode is previously turned off, the mode may be turned on, and vice versa.

As will be discussed herein, if the sip/puff mode is turned off, any Y-axis component of any movement input may be used to cause the microscope camera to move along a Z axis (e.g., closer or farther from the patient) for focus-only modification. X-axis components of movement inputs may not have an effect on the controller when the sip/puff mode is turned off. However, if the sip/puff mode is turned on, movement inputs may cause the controller to cause the microscope camera to move in an XY direction.

Thus, if a Cartesian movement input is received, the processor may determine whether the sip/puff mode is on (block 808). If received, the processor may determine the Y-axis component of the received input (e.g., a Y-component of the vector representing the movement of joystick 702) (block 810). The processor may cause corresponding movement of the DSM head 110 (e.g., proportionate to the scale of the Y-component) (block 812).

If the sip/puff mode is on, the processor may determine whether a pressure is detected (block 814). In some embodiments, if no pressure is detected, the controller may take no action on the DSM head 110, for example, to protect against inadvertent movements of the joystick. If pressure is detected, the processor may determine whether there is a positive or negative air pressure (block 816). For example, one or more sip/puff detectors 703 may detect a negative pressure (a "sip"), caused by a sipping of air from the tube of the joystick 702 by the surgeon. Alternatively, the one or more sip/puff detectors 703 may detect a positive pressure (a "puff"), caused by a blowing of air into the tube of the joystick 702 by the surgeon, If a positive pressure is detected, the processor may cause corresponding Cartesian movement of the DSM head and may pivot the DSM head about a focal point (block 818). In some aspects, the focal point may be based on the final destination of the resulting movement. If a negative pressure is detected, the processor may just cause corresponding Cartesian movement of the DSM head (block 820). For example, while traditional microscopes may allow angular pivots by causing constraints to certain axes or axis combinations linearly, such pivots are ineffective as the pivot point that is most desirable by the surgeon is typically at the surgical site where needed. The DSM head's x-y pivoting, as described in block 818, allows for pivoting about the microscope's focal point, and is thus more desirable.

In some embodiments, various movement amounts may be limited per input to prevent accidental large movements. For example for intended movements of the DSM head 110 along the Z-axis (e.g., relative to on screen), the DSM head 100 may be restricted in the distance it moves per input or per time (e.g., only 4 mm at a time per press of the joystick in the Y-axis direction when the sip/puff mode is off). Thus, if the surgeon were to accidentally bump the joystick down and the joystick were to remain in a downward state as a result, the DSM head 100 may be prevented from moving downward more than 4 mm. To continue moving the microscope downward, the surgeon may be required to return the joystick to a neutral position.

Conclusion

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A system for controlling a surgical visualization system, the system comprising:
   a microscope camera associated with the surgical visualization system;
   a controller of the microscope camera, wherein the controller is separate from the microscope camera, wherein the controller comprises a joystick and a pressure detector, wherein the joystick comprises a tube to facilitate air flow, wherein the pressure detector is configured to detect pressure in the tube;
   a processor; and
   a memory storing instructions that, when executed by the processor, cause the processor to:
      receive a movement input based on a movement of the joystick along a Cartesian direction;
      detect, via the pressure detector, a negative pressure in the joystick caused by a sipping of air from the tube;
      cause a corresponding movement of the microscope camera along the Cartesian direction;
      receive, via the controller, a second movement input based on a second movement of the joystick along a second Cartesian direction;
      detect, via the pressure detector, a positive pressure in the joystick, based on a puffing of air into the tube; and
      cause a corresponding second movement of the microscope camera along the second Cartesian direction and a pivot of the microscope camera about a focal point at a destination of the corresponding second movement.

2. The system of claim 1, wherein the instructions, when executed, further cause the processor to:
   detect, via the pressure detector, a double negative pressure in the joystick caused by a double sipping of air from the tube; and
   cause the controller to deactivate a sip/puff mode.

3. The system of claim 2, wherein the instructions, when executed, further cause the processor to:
   receive, via the controller, a third movement input based on a third movement of the joystick of the controller along a third Cartesian direction, wherein the third movement along the third Cartesian direction includes a Y-axis component;
   determine a scalar and a direction of the Y-axis component; and
   cause a third movement of the microscope camera along a Z-axis, wherein a distance of the third movement of the microscope camera is proportional to the scalar of the Y-axis component, wherein a direction along the Z-axis corresponds to the direction of the Y-axis component.

4. The system of claim 3, wherein the third movement of the microscope camera along the Z-axis moves the microscope camera towards or away from a field of view.

5. The system of claim 2, wherein the instructions, when executed, further cause the processor to:

detect, via the pressure detector, a second double negative pressure in the joystick caused by a second double sipping of air from the tube; and cause the controller to reactivate the sip/puff mode.

6. The system of claim 2, wherein activating the sip/puff mode causes the controller to perform commands after detecting positive pressure in the joystick, and wherein deactivating the sip/puff mode causes the controller to ignore any X-component of any received movement inputs.

7. The system of claim 1, further comprising:

a keyed proximity detector attached to the controller; and an antenna or a QR code on a user of the controller;

wherein the instructions, when executed further cause the processor to:

detect, based on the antenna or the QR code being within a predetermined distance to the keyed proximity detector, a presence of the user; and activate the controller to receive user input.

8. The system of claim 1, wherein the microscope camera is further associated with an integrated surgical navigation and visualization system, wherein the integrated surgical navigation and visualization system includes the surgical visualization system.

\* \* \* \* \*